United States Patent
Taylor et al.

(10) Patent No.: US 10,391,136 B2
(45) Date of Patent: Aug. 27, 2019

(54) LENTIL CONSUMPTION REDUCES ARTERY REMODELING AND RESTORES ARTERIAL COMPLIANCE

(71) Applicant: Prairie Skyline Ventures, Winnipeg (CA)

(72) Inventors: Carla G. Taylor, Winnipeg (CA); Peter Zahradka, Winnipeg (CA)

(73) Assignee: Prairie Skyline Ventures, Winnipeg, Manitoba (CA)

(*) Notice: Subject to any disclaimer, the term of this patent is extended or adjusted under 35 U.S.C. 154(b) by 17 days.

(21) Appl. No.: 15/738,956

(22) PCT Filed: Jun. 27, 2016

(86) PCT No.: PCT/CA2016/050749
§ 371 (c)(1),
(2) Date: Dec. 21, 2017

(87) PCT Pub. No.: WO2016/205954
PCT Pub. Date: Dec. 29, 2016

(65) Prior Publication Data
US 2018/0169167 A1    Jun. 21, 2018

Related U.S. Application Data

(60) Provisional application No. 62/184,307, filed on Jun. 25, 2015.

(51) Int. Cl.
*A61K 36/48* (2006.01)
*A61P 9/12* (2006.01)

(52) U.S. Cl.
CPC .............. *A61K 36/48* (2013.01); *A61P 9/12* (2018.01)

(58) Field of Classification Search
CPC ........................................... A61K 36/48
See application file for complete search history.

(56) References Cited

FOREIGN PATENT DOCUMENTS

WO    WO-2010102402 A2 *   9/2010   ............ A61K 36/48

OTHER PUBLICATIONS

Benefits of Masoor dal (lentils), Sneha's Recipe, The Good Food Guide, https://snehasrecipe.blogspot.com/2014/02/benefits-of-masoor-dal-lentils.html, 2014.*
Hanson, M. et al., "Abstract 18985: Lentil-based diets reduce vascular remodeling through a p38 mitogen-activated protein kinase dependent mechanism in the spontaneously hypertensive rat", Circulation, Nov. 26, 2013, vol. 128 (Suppl. 22) [http://circ.ahajournals.org/content/128/Suppl_22/A18985].
Thompson, T. and Peters, B., "New study shows eating pulses every day improves blood vessel function and fights heart disease", Pulse Canada, Apr. 20, 2009 [http://www.pulsecanada.com/uploads/74/77/74773e655c7bb38aac14ed3537f864210/09-04-20-EB-release.pdf].

* cited by examiner

*Primary Examiner* — Rosanne Kosson
(74) *Attorney, Agent, or Firm* — Michael R. Williams; Ryan W. Dupuis; Ade & Company Inc.

(57) ABSTRACT

It is demonstrated herein that the consumption of a composition prepared from lentil hulls changes the elastic properties of vessel walls. This means that administration of an effective amount of the composition over a suitable period of time lentils can reverse vascular remodeling, thereby restoring arterial compliance, whereas it was previously assumed that arterial remodeling was irreversible.

18 Claims, 6 Drawing Sheets

(a)

(b)

LENTIL CONSUMPTION REDUCES ARTERY REMODELING AND RESTORES ARTERIAL COMPLIANCE

PRIOR APPLICATION INFORMATION

The instant application claims the benefit of US Provisional Patent Application Ser. No. 62/184,307, filed Jun. 25, 2015.

BACKGROUND OF THE INVENTION

Hypertension affects more than 1 In 5 adults in North America[1] and its prevalence is increasing as a result of the obesity epidemic and the ageing population.[2,3] Over time, hypertension damages organs such as the brain, eyes, heart, and kidneys, with resistance arteries considered to be the first organ affected.[4,5] Resistance arteries, those arteries smaller than 350 µm, are important in regulating blood flow and preventing a fluctuating pressure environment in the organs distal to the arterial beds.[6] Damage to the resistance arteries comes in the form of remodeling and is caused by increased shear and tensile stresses resulting in decreased arterial distensibility and compliance, a process termed arterial stiffening.[3,7]

Like hypertension, arterial remodeling and stiffening are largely asymptomatic until late stages when they affect organ function and ambulation.[8] Vascular remodeling in essential hypertension, which accounts for more than 90% of diagnoses,[9] generally takes the form of eutrophic inward remodeling.[10] Eutrophic Inward remodeling decreases the lumen and external diameters, without changing the media cross-sectional area, leading to higher media:lumen ratio (M:L).

Hypertension diagnoses typically requires polypharmacy to manage the pressure and associated complications,[11] and usually combines a diuretic to decrease the circulating volume and pressure with an angiotensin converting enzyme (ACE) inhibitor that decreases anglotensin II (AngII) production and its sequelae, namely vasoconstriction, fluid retention and cellular hypertrophy. However, there is an increasing emphasis being placed on diet and exercise to help manage hypertensive patients. Within this context, research on pulse crops has revealed that consumption of dried beans, peas, lentils and chickpeas can provide benefits with respect to cardiovascular health.[12-16] Rimm et al[12] showed that a daily serving of peas reduced the relative risk of heart attack to 0.52 (95% Cl 0.31-0.88), while Bazzano et al[13] Indicated that eating 4 servings of pulses a week, compared to 1 or fewer, reduced the risk of coronary heart disease and overall cardiovascular disease by 22% and 11%, respectively. Additionally, there is evidence that pulses and pulse extracts may decrease vascular remodeling[17,18] in response to AngII,[15] even inhibiting ACE directly.[14,19]

The spontaneously hypertensive rat (SHR) is a well-established and widely used model of hypertension,[20] experiencing marked increases in both blood pressure (BP) and arterial stiffness.[21] SHR exhibit increased expression of hypertrophic mediators such as profilln-1 (PFN1) and ACE,[22,23] and activation of p38 mitogen-activated protein kinase (p38MAPK) and extracellular signal-regulated kinase 1/2 (ERK1/2) in response to the chronic hypertensive state.[24,25]

SUMMARY OF THE INVENTION

According to a first aspect of the invention, there is provided a method for restoring arterial compliance in an individual in need of such treatment, said method comprising administering to the individual an effective amount of a composition comprising lentil hulls prepared from whole lentils or milling fractions.

Arterial compliance can be defined as the action in which an artery yields to pressure or force without disruption. Alternatively, arterial compliance can be considered to be the elasticity of arteries. As will be appreciated by one of skill in the art, arterial stiffness decreases arterial compliance.

According to a further aspect of the invention, there is provided use of a composition comprising lentil hulls for restoring arterial compliance.

According to another aspect of the invention, there is provided a composition comprising lentil hulls prepared from whole lentils or milling fractions for restoring arterial compliance in an individual.

According to a first aspect of the invention, there is provided a method for preparing a medicament for restoring arterial compliance in an individual in need of such treatment, said method comprising admixing an effective amount of a composition comprising lentil hulls prepared from whole lentils or milling fractions with a suitable pharmaceutically acceptable excipient.

Specifically, as discussed herein, the inventors have surprisingly found that administration of a composition comprising lentil hulls is able to restore arterial compliance in an individual in need of such treatment.

As discussed herein, administration of an effective amount of a composition comprising lentil hulls for a period of time restores arterial compliance. Subsequently, once arterial compliance has been restored in the individual, the composition comprising hulls is administered to the individual on a dosage schedule as a maintenance dose. In some embodiments, the maintenance dose is a lower amount than the effective amount administered previous, as discussed herein.

As will be appreciated by one of skill in the art, an effective amount of composition comprising the lentil hulls must be administered for the benefits to be seen, as discussed herein. Accordingly, the composition comprising lentil hulls may be prepared in a variety of ways. For example, lentils can be dehulled and the hulls ground into a powder via several different approaches to establish a specific particle size, without and without pretreatments such as soaking and heating. Alternatively, whole lentils can be ground into a powder or whole lentils can be milled and separated into milling fractions and the milling fractions containing lentil hulls are administered, also with or without pretreatment. In these embodiments, the amount of lentil hull powder in either the whole lentil powder or the milling fraction can be determined or estimated based on the percentage of the powder or fraction that is from the hulls. This can then be used to determine the effective amount. For example, 1 g of whole lentil powder that was 10% hulls contains 100 mg of lentil hull powder.

The composition comprising lentil hulls can be administered to the individual or subject, for example, a human patient, by a variety of means, as discussed herein. For example, the lentil hull containing powder can be ingested directly as a powder or the powder can be suspended in a liquid vehicle which is then administered to or ingested or swallowed by the patient. As will be apparent to one of skill in the art, a variety of suitable liquid vehicles may be used, depending on the preference of the individual. Furthermore, the composition does not necessarily need to be completely dissolved in the liquid vehicle for administration. Alternatively, the powder can be formulated into capsules or tablets. In yet other embodiments, the lentil hull containing powder can be added to a food product, for example, added during preparation of the food product or added to the finished food product prior to consumption.

As discussed herein, the effective amount of the composition comprising lentil hulls must be administered to the individual in need of such treatment, that is, an individual suffering from arterial stiffness, for a suitable period of time for arterial compliance to be restored. Following this, a lower maintenance dose of the composition comprising lentil hulls may be administered to the individual. It is important to note that the individual may be administered the lentil hulls in any of the various forms described herein, for example, as a powder made from lentil hulls, from whole lentils or from a lentil milling fraction comprising the hulls. Furthermore, the powder may be arranged or formulated to be administered as a capsule, tablet or other similar dosage form or may be suspended in a liquid vehicle as discussed herein or may be used as a food ingredient as discussed herein.

DESCRIPTION OF THE PREFERRED EMBODIMENTS

Figure 1:
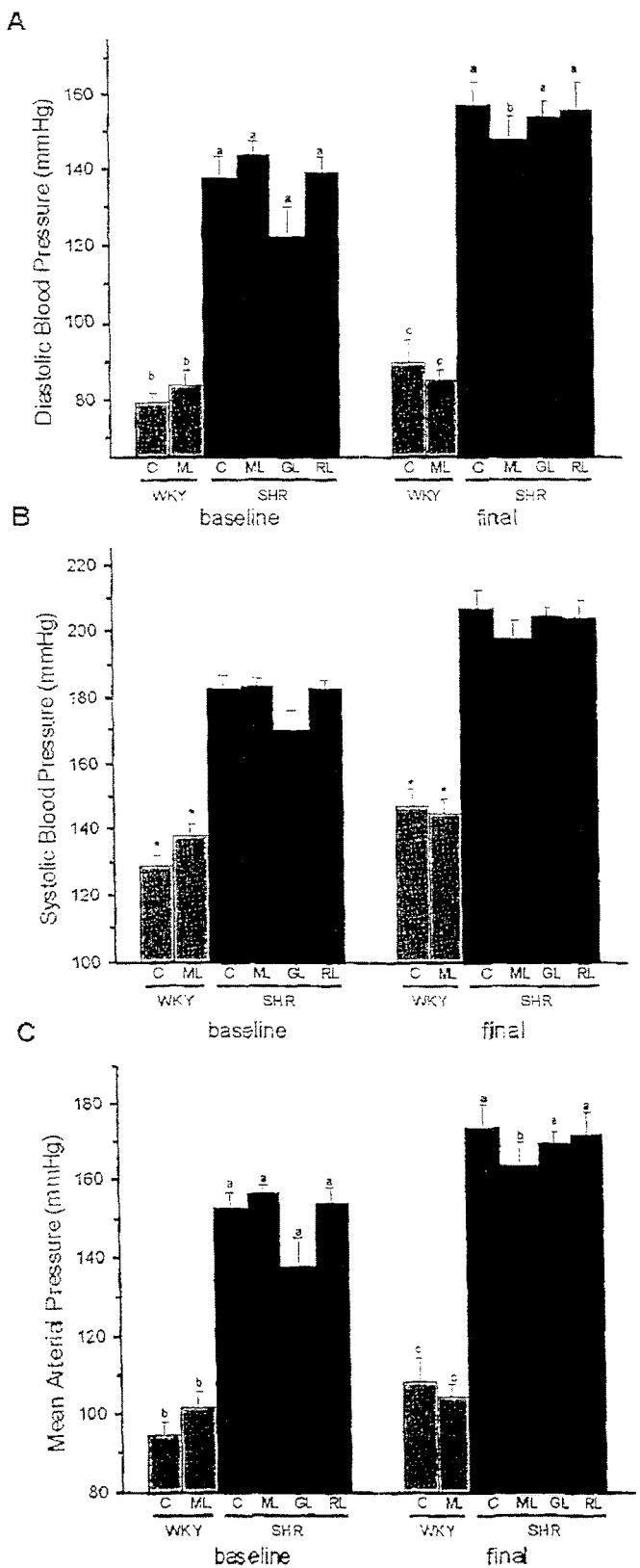
FIG. 1. Blood pressure. A) Diastolic blood pressure (DBP), B) Systolic blood pressure (SBP), and C) Mean arterial pressure (MAP) were measured at baseline and 8 weeks. Data are expressed as means±SE (n=9-10/group). Bars with different letters are significantly different ($P<0.05$).

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

We have previously shown that a lentil-based diet was able to attenuate the age-related rise in blood pressure as well as alter aortic remodeling in the SHR.[18]

Specifically, it was shown that a lentil-based diet was able to attenuate the rise in blood pressure experienced by the SHR model to the greatest extent. Vascular remodeling is a common morphological response to chronic hypertension, wherein a more muscular vessel wall is required to pump blood into the higher pressure environment in the arteries. This remodeling causes arterial stiffness, as discussed herein. The vessel walls of the animals fed the lentil based diet did not thicken to the same degree as the control hypertensive animals. This suggested that the lower blood pressure prevented wall thickening.

This study was designed to determine whether the attenuation of arterial remodeling would also be seen in smaller, resistance arterioles, and which of red or green lentils elicits a better response. However, as discussed herein, it was surprisingly found that (i) a reduction in blood pressure may not always occur, (ii) the lower blood pressure is not the cause of the change in vessel wall properties and (iii) the change in vessel wall structure changes the elastic properties of the vessel wall. That is, surprisingly, it has been found that the consumption of lentils, for example lentil hulls, affects the vessel wall directly. This means that administration of lentils can reverse vascular remodeling, thereby restoring arterial compliance. As will be appreciated by one of skill in the art, this is highly surprising as previously it was assumed that arterial remodeling was irreversible.

Hypertension is a major driving force behind arterial remodeling, increasing stiffness, and decreasing compliance and function. Pharmaceutical relief is capable of lowering high blood pressure for some individuals, but typically this does not affect arterial remodeling. Furthermore, polypharmacy can also be required to manage symptoms and complications. Our initial studies established that lentils were able to significantly attenuate the development of hypertension in SHR rats. The current study examined the hypothesis that the positive actions of lentils on blood pressure are mediated through direct changes in arterial function that decrease remodeling and improve arterial compliance.

As discussed below, seventeen-week SHR were randomly assigned to groups (n=10/group) fed (i) 30% w/w green lentils, (ii) 30% red lentils, (iii) 30% mixed lentils (red and green), or (iv) no lentils for 8 weeks. Normotensive Wistar Kyoto (WKY) groups (n=10/group) received either the mixed lentil or no lentil diet. Blood pressure, pulse wave velocity (PWV) and pressure myography were measured. There were no dietary related changes in PWV. Mixed lentils, but not green or red lentils, attenuated the rise of diastolic blood pressure and mean arterial pressure in SHR. Both red and green lentils improved arterial compliance and reduced stiffness of SHR, with green lentils having the greatest effect. All lentil diets reduced the media:lumen ratio to a level between control-fed SHR and WKY.

As discussed below, lentil-based diets suppress pathological vascular remodeling in SHR, while green lentils can restore vascular compliance to the level of normotensive WKY in the absence of a decrease in blood pressure.

Consumption of a lentil-rich diet by SHR reversed the pathological remodeling of the arteries that is caused by hypertension as indicated by a decrease in the media:lumen ratio, which was paralleled with an increase in arterial compliance (or decrease in arterial stiffness), in the absence of a change in blood pressure or lipid profile.

Specifically, as discussed below, inclusion of lentils in the diet of SHR reduced the media:lumen ratio by 21% and arterial stiffness by 24 to 34% in the absence of a change in blood pressure. Concomitant changes in PWV were not observed.

The ability to improve arterial elasticity and/or restore arterial compliance through lentil consumption indicates that a simple dietary intervention, for example, in the form of a food ingredient or food additive, supplement and/or capsule, can be used to reduce the risk of mortality and morbidity from cardiovascular disease by altering the structural properties of arteries. As will be appreciated by one of skill in the art, this is an ideal solution to treating the major underlying cause of cardiovascular disease.

Specifically, arterial stiffness is a consequence of biological aging and arteriosclerosis. Increased arterial stiffness is associated with an increased risk of cardiovascular events such as myocardial infarction and stroke as well as other cardiovascular diseases. Arterial stiffness can be caused by many factors, for example but by no means limited to aging, high blood pressure, smoking, high cholesterol, obesity, lack of exercise, poor diet and excessive alcohol consumption.

Arterial stiffening, or a decrease in the ability of an artery to distend, is typically caused by structural changes in the components of elastic artery walls that result in an alteration in the ratio of collagen to elastin[39-42]. Elastic arteries, which bear the majority of the load offered to the systematic vasculature by the heart, must have the ability to both expand and to subsequently recoil, thereby ensuring steady flow delivery to the rest of the body[43], while stiff arteries not only deliver a damaging pulsatile flow, they also increase the energy demands on the heart that in turn result in cardiac hypertrophy. Accordingly, a number of important cardiovascular (CV) risk factors have a strong association with arterial stiffening[44-47] Assessment of arterial stiffness typically falls into one of 2 groups: (i) Measurement of arterial elasticity and (ii) Physical measurement of arterial structural parameters.

The techniques used to assess arterial elasticity include (I) pulse wave velocity (PWV), which gives a direct idea of arterial stiffness by recording the time for blood to flow over a specified distance, and (ii) pulse wave analysis (PWA), which utilizes an algorithm to calculate the augmentation index (AIx) based on the shape of the arterial pressure waveform. Both methods provide an estimate of central aortic values, which are thought to be better predictors of CV disease and outcomes[48]. Together, these are referred to as "functional stiffness" parameters[49]. The most widely accepted (i.e. gold-standard) method of determining arterial stiffness is carotid-femoral (cf-) PWV[51] for which reference and normal values have recently been published[53, 54]. It is typically accepted that arteries are stiff where cf-PWV>10 m/s. This value, however, does not reflect differences due to aging, thus algorithms have been developed to define stiffness with respect to age[54]. Recently, brachial-ankle (ba-) PWV has become a popular alternative to cf-PWV since it does not require handling of the groin area. Furthermore, the equipment for measuring ba-PWV is automated, thus decreasing the contribution of subjectivity and operator technique to the measurement. Reference standards have also been determined for this procedure, however, the values are higher for ba-PWV than those seen with cf-PWV. It has been suggested that arterial stiffness is present when ba-PWV>18 m/s [Saji 2015, Munakata 2015], although threshold values of 14 and 21 m/s have also been suggested [Xu 2008]. In contrast to PWV, PWA provides an AIx that is based on reflection of the pulse wave, and thus is derived mathematically from parameters that are linked to the speed of pulse wave propagation in the circulatory system. The AIx is often reported after normalization to heart rate, since heart rate is a factor in the algorithm. Therefore, the value is typically reported as AIx@75 bpm. The threshold for stiffness is dependent upon the instrument used to obtain this value, however, for the most commonly used and best studied system, the SphygmoCor, AIx@75>40% is indicative of arterial stiffness [Shiburi 2006]. It is important to recognize that even though these values are based on quite distinct formulae and operational techniques, each of these measurements has been directly linked with CV morbidity and mortality[55-58].

Endothelial dysfunction is a condition wherein the cells lining the artery wall become unable to respond to shear stress as a result of changes in blood flow, and this in turn affects arterial tone which can be detected as a decrease in arterial elasticity (or greater arterial stiffness). It is possible to measure endothelial dysfunction via reactive hyperemia (RHI), or the ability of an artery to respond to a brief period of ischemia[59]. The most effective method for measuring this parameter is flow-mediated dilatation (FMD), which employs ultrasound to determine the dimensions of the brachial artery lumen before, during and after a 5 minute occlusion. While the correlation of FMD with endothelial dysfunction is excellent, the technical skills required for this procedure have kept it from being routinely used. As a result it cannot be used as a diagnostic to discriminate between healthy and stiff arteries based on a single measurement threshold [Sejda 2005].

With respect to measuring the physical properties of the blood vessels, it is possible to examine its "material stiffness"[49]. This approach examines changes in artery diameter in response to the pulse wave or another stimulus (either a hormone or pressure), thus providing indices such as arterial distensibility and arterial compliance[50-52]. However, such methods are not applicable to humans since they require samples of blood vessels for testing. Finally, although it is not a measurement of stiffness per se, endothelial dysfunction affects the processes that regulate arterial tone and thus can both simulate and promote arterial stiffness [McEnlery 2006]. Methods that are clinically useful in this regard include a variety of imaging techniques that measure either the arterial wall thickness or the lumen diameter, or a combination of both. These methods include the use of ultrasound to examine the intimal-media thickness of the carotid artery, as well as computed tomography, magnetic resonance, intravascular ultrasound, supersonic shear imaging, high frame rate ultrasound, tissue Doppler Imaging, and imaging of arterial calcification, all of which can be used to view the morphology and responsiveness of the artery wall.

As discussed herein, there is provided a method for restoring arterial compliance as indicated by both structural and functional changes to the blood vessel wall in an individual in need of such treatment, said method comprising administering to the individual an effective amount of a composition derived from a lentil powder containing hulls prepared from whole lentils or milling fractions of whole lentils.

For example, the composition may comprise hulls (isolated by the dehulling of lentils) which have been ground or may comprise whole lentils which have been ground wherein at least 5% or at least 7% of the ground material comprises ground hulls as discussed herein.

According to a further aspect of the invention, there is provided use of a composition derived from lentil powder hulls for restoring arterial compliance.

According to another aspect of the invention, there is provided a composition comprising lentil hulls prepared from whole lentils or milling fractions for restoring arterial compliance in an individual.

According to a first aspect of the invention, there is provided a method for preparing a medicament for restoring arterial compliance in an individual in need of such treatment, said method comprising admixing an effective amount of a composition comprising lentil hulls prepared from whole lentils or milling fractions with a suitable pharmaceutically acceptable excipient.

As discussed herein, administration of an effective amount of a composition derived from or comprising lentil hulls for a period of time restores arterial compliance. That is, the composition must be administered for a period of time at the effective amount to have a detectable effect on arterial compliance. Subsequently, a composition comprising lentil hulls is administered on a dosage schedule as a maintenance dose.

As will be appreciated by one of skill in the art, an effective amount of the lentil hulls must be administered for the benefits to be seen, as discussed herein. Accordingly, the composition derived from lentil hulls may be prepared in a variety of ways. For example, lentils can be dehulled and the hulls ground into a powder. Alternatively, whole lentils can be ground into a powder or whole lentils can be milled and separated into milling fractions and the milling fractions containing lentil hulls are administered. In these embodiments, the amount of lentil hull powder in either the whole lentil powder or the milling fraction can be determined or estimated based on the percentage of the powder or fraction that is from the hulls. This can then be used to determine the effective amount. For example, 1 g of whole lentil powder that was 10% hulls contains 100 mg of lentil hull powder.

As will be known by those of skill in the art, it is standard practice in the industry to dehull lentils before packaging and shipping for human consumption.

However, as discussed herein, the composition derived from lentil hulls is selected from the group consisting of a powder prepared from lentil hulls; a powder prepared from whole lentils; and a powder prepared from a lentil milling fraction that includes lentil hulls.

In the examples provided below, green lentils had the greatest effect. However, various lentil varieties for example but by no means limited to green, red, brown, yellow and black or mixtures thereof, may be used within the invention.

The composition derived from lentil hulls can be administered to the individual or subject, for example, a human patient, by a variety of means, as discussed herein. For example, the lentil hull containing powder can be ingested directly as a powder or the powder can be suspended or dissolved in a liquid vehicle which is then administered to or ingested by the patient. Alternatively, the powder can be formulated into capsules or tablets. In yet other embodiments, the lentil hull containing powder can be added to a food product, for example, added during preparation of the food product or added to the finished food product prior to consumption. As will be apparent to one of skill in the art, there are a wide variety of food products in which the composition of the invention can be incorporated as an ingredient.

Methods for processing lentil are well known in the art. For example, a variety of wet and dry methods are known for dehulling of lentils. Typically, this involves loosening the hull and then removing the hull. Alternatively, hulls can be removed, basically, worn away, for example, by an abrasion-type hulling machine.

Alternatively, whole lentils can be milled and separated into fractions. Methods for milling lentils are well-known in the art and include methods such as for example impact milling, attrition milling, knife milling and direct pressure milling. Once the lentils have been milled, the ground lentils can be separated into fractions using means known in the art.

Similarly, methods of preparing lentils are well known in the art and as such a variety of these methods may be used within the invention.

For example, in one embodiment, a quantity of isolated lentil hulls are prepared by rinsing the hulls, drying the hulls and then adding water at a 3:1 ratio of water to dried hulls. The hulls are then cooked until soft, for example for approximately 11 minutes. The cooked material is then drained to remove the cooking water and the drained material is freeze dried.

A similar process can be used for the preparation of whole lentils. For example, the lentils are rinsed and then water is added at a 3:1 ratio of water dry pulse. The whole lentils are then cooked until the desired softness is attained, for example, for 30-45 minutes. The cooked material is then drained to remove the cooking water and the drained material is freeze dried.

In some embodiments, the lentils, either whole lentils, lentil hulls or lentil milling fraction, are cooked in a food grade facility. Cooking is required to inactivate any anti-nutritional factors. Following freeze-drying, the freeze dried material is made into a powder. It is noted that a variety of methods for producing a powder are well known in the art, as discussed above.

For example, if the primary source of powder is green lentils, it is of note that green lentils are typically not processed and are primarily used whole. Consequently, industrial facilities for dehulling green lentils thus do not exist at present. Accordingly, lentil hulls from green lentils were prepared using pilot facilities present at the Canadian International Grains Institute (CIGI) in Winnipeg. The lentils were loaded into a hopper connected to a Buhler (Uzwil, Switzerland) model MJSG 67C stone dehuller (pilot scale). Subsequently, the hulls were separated from the cotyledons using a Buhler model MVSG-60 aspiration channel. For example, in order to efficiently separate the lentil hulls from the cotyledon and leave the cotyledon intact required appropriate adjustments to the rate of flow and degree of aspiration, as well as adjustments for the size of the cotyledons. This process produces hulls considered acceptable for preparation of the lentil powder as discussed herein. It is of note that other suitable methods may be used to prepare a suitable composition in accordance with the invention.

As discussed herein, the experiments that showed lentils contain a bioactive material capable of affecting arterial function was initially done at a laboratory scale using processes involving sequential cooking, freeze drying and milling to produce the powder. Since each of these steps may have limitations with respect to commercial scale-up, the effect of these treatments on the properties of the powder was examined. In total, 8 variations were tested, including various combinations of heating/no heating, freeze-drying/extrusion, and soaking/no soaking. After these treatments, all samples, including the control hulls provided for the tests, were milled using a Perten mill model 3600 with disk #5. These tests examined two factors, one physical and one chemical—particle size and antioxidant activity (see Table 6). Extrusion provided finer powder than freeze-drying. It also maintained higher levels of antioxidant activity. Also, the finer powder had more antioxidant activity than an equivalent amount of coarser powder. The antioxidant activity is a good indication of the polyphenolic content of the hull which is responsible for the biological activity that has been observed.

For example, the lentil powder can be used as an ingredient for the enrichment of food products or can be taken directly as a powder. Alternatively, the whole lentil powder can also be encapsulated or otherwise formulated and/or prepared for administration as a capsule or tablet.

As discussed herein, the daily dosage of the powder obtained from lentil milling fractions is much less than a typical serving of lentils. Furthermore, the bulk of the starch and soluble fibre may have been removed which eliminates the typical side-effects observed with increased consumption of pulses such as bloating and gas.

In other embodiments, the effective amount may be 250 mg-1 g of lentil hull powder.

In some embodiments, the lentil powder is administered to the individual on a treatment regimen wherein 250 mg-1 g is administered to the individual daily for a period of 4-12 weeks.

That is, the effective amount of the lentil hull powder is administered for period of time, for example, 28 consecutive days, 35 consecutive days or 42 consecutive days or any other suitable period of time until arterial compliance has been restored which can be determined by a variety of means, as discussed herein.

Optionally, once arterial compliance has been restored, the individual may then be administered a maintenance dose, as discussed herein.

As will be apparent to one of skill in the art, the lentil powder may be administered in a daily unit dose of 250 mg to 1 g or may be administered as two or more doses over the course of the day.

For example, the hulls may be approximately 7-10% of the whole lentil powder, so consuming a minimum of 2 tbsp (~30 ml) or 30 capsules (1 gm per capsule) daily is required. An equivalent dose of a milling fraction may be less, although it would depend on the relative amount the fraction represents of the whole seed. These amounts are considerably less than the daily serving size recommended in Canada's Food Guide for Healthy Eating, where a single serving of whole lentils consists of ¾ cup (12 tbsp).

A maximum dose for treatment may be for example twice this amount, whereas a maintenance amount would be ¼ the minimum dose needed to obtain an effect for treatment purposes. As will be appreciated by one of skill in the art, this is based on the assumption that this dose is defined for a normal 70 kg human, and so the dosage may be adjusted accordingly.

The difference between these embodiments is the presence of soluble fibre (in the whole lentil powder), which may provide additional benefits to health for example although by no means limited to the lowering of cholesterol levels.

According to an aspect of the invention, there is provided a method for reducing arterial stiffness comprising administering to an individual in need of such treatment an effective amount of a lentil powder.

According to another aspect of the invention, there is provided use of a lentil powder for reducing arterial stiffness. Since the lentil dose may be capable of lowering diastolic blood pressure by 2-10 mmHg, this invention may also be used for the treatment of hypertension.

The lentil powder is made either from whole lentils as described above or is made from lentil milling fractions only, referred to herein as a lentil powder.

In some embodiments, the lentil powder is a lentil milling fraction powder. The powder may be defined as flour based on fineness, or it could be bumped, flaked or kibbled. The powder may be derived from wet or dry milling, and include only a single fraction or consolidation of several fractions.

In some embodiments, an individual in need of such treatment is an individual who is a senior, and thus would be more prone to having multiple chronic conditions in addition to cardiovascular disease, such as for example diabetes, hypertension, hyperlipidemia, obesity, rheumatoid arthritis, chronic kidney disease and renal dysfunction. As used herein, the term "senior" may refer to a person who is 55 years or older, 60 years or older or 65 years or older.

In addition, an individual in need of such treatment may be any individual suffering from multiple chronic conditions such as for example cardiovascular disease as well as diabetes, hypertension, hyperlipidemia, obesity rheumatoid arthritis and renal dysfunction, regardless of age.

Treatment options for this population typically involve polypharmacy since different drugs are required to manage each of the conditions that are present. It is of note that the lentil powder described herein act through mechanisms which are not currently targeted by the various drugs designed for this array of conditions. Consequently, there is no indication that an interaction will occur with any of the drugs currently in use and thus the lentil powder can safely be used in a combination therapy. Since there is no known pharmaceutical capable of improving arterial stiffness, the product will also be a useful adjunct to other medications being employed to manage cardiovascular disease risk or symptoms that manifest after a cardiovascular event (e.g. heart attack, stroke).

Alternatively, an individual in need of such treatment may be an individual who has a ba-PWV above 18 m/s or above 14 m/s or a cf-PWV above 10 m/s or a AIx@75 value of greater than 40% or any individual determined to have or diagnosed with or considered to be at risk of having low arterial compliance.

In some embodiments, the effective amount is an amount that is sufficient to reduce arterial stiffness or restore arterial compliance in an individual in need of such treatment.

As will be appreciated by one of skill in the art, this initial treatment may be stopped once the individual being treated has a ba-PWV below 18 m/s or 14 m/s or an AIx@75 value of less than 40% or cf-PWV less than 10 m/s. Alternatively, imaging showing changes of more than 5% reduction in medial thickness, lumen diameter or media-lumen ratio would also indicate the treatment could be stopped.

In some embodiments, following the initial treatment regimen, the individual is administered a maintenance dose of 125-500 mg of lentil hull powder. This maintenance dose may be administered daily. Comparative doses of whole lentil powder or milling fraction powder can be calculated as discussed herein.

As will be appreciated by one of skill in the art, as used herein, "daily" does not necessarily mean every day and may mean substantially every day, for example 7 out of 10 days or even every other day, provided that ba-PWV and AIx@75 values remain acceptable.

As discussed below, this study has shown that consumption of green lentils by SHR can restore arterial compliance to the levels of control WKY, with a smaller improvement also seen with feeding red lentils. As a result of these changes, there were significant improvements in arterial stiffness as shown by the elastic modulus versus isobaric stress measurements. These effects of lentil feeding on vascular properties occurred under conditions where blood pressure was not altered, in agreement with previous studies that have indicated arterial remodeling is not dependent on the reduction of blood pressure.[6,10] On the other hand, arterial remodeling in the lentil-fed SHR groups was associated with a decrease in activated p38MAPK, which is known to influence cell growth and extracellular matrix production,[30,31] while the positive changes in arterial compliance occurred independent of LDL-C levels and other physiological and biochemical parameters.

Figure 2:
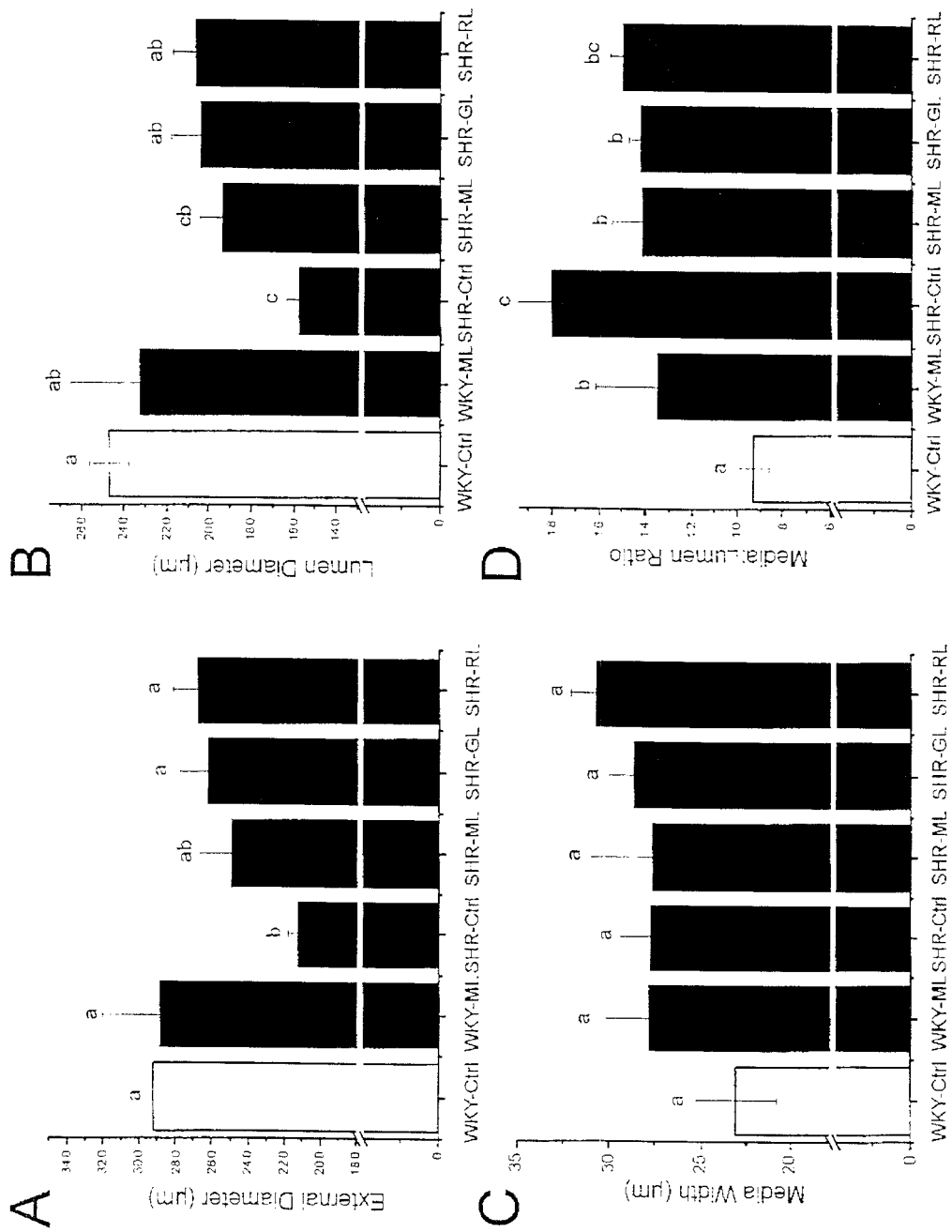
FIG. 2. Vascular geometry measurements of mesenteric arteries calculated from data obtained at 45 mmHg on the pressure myograph. A) External diameter and B) Lumen diameter C) Media width and D) Media:lumen ratio. Data are expressed as means±SE (n=6-7/group). Bars with different letters are significantly different ($P<0.05$).

Arterial compliance is important in buffering pressure fluctuations in the vasculature, thus maintaining constant blood flow to all organ systems. Vascular remodeling due to hypertension decreases arterial compliance, which perpetuates hypertension and contributes to the organ damage that occurs in a chronic hypertensive state. Morphometric analysis showed the M:L ratio was significantly reduced in both SHR-ML (−22%) and SHR-GL (−21%) compared to SHR-Ctrl (FIG. 2). Red lentils reduced the M:L ratio by 17% In the SHR-RL group compared to SHR-Ctrl. For all three groups, the changes in M:L ratio were a reflection of an increase in lumen diameter and not media width. Taken together, the increased lumen size and external diameter indicate that there is an increase in the medial area (i.e. hypertrophy), even if the media width remains unchanged. Histological staining of the arteries revealed that an increase in cell size likely accounts for the larger media in SHR compared to WKY (Table 1). However, although the M:L ratio declined in the mixed and green lentil-fed SHR groups due to a change in the lumen diameter, medial smooth muscle cell size remained the same. These results suggest a non-cellular component that is unaffected by diet contributes to medial hypertrophy of the blood vessel wall. In SHR, there were no significant changes in either collagen or elastin relative to WKY, thus implying these extracellular proteins were not involved. Rather, the apparent but non-significant decline in collagen content relative to the nsECM (non-collagen/non-elastin staining ECM) of the arterial wall suggests that collagen is being replaced by another extracellular component. Given the close connection between p38MAPK and ECM production and degradation,[30,32,33] this component may be a distinct ECM protein, matrix metalloproteinase-degraded collagen or a combination of both. The observed absence of hyperplasia is in agreement with several published studies and contrasts with several others. It has been suggested the type of vascular response to stress that occurs is dependent upon the vascular bed from which the vessels are obtained.[34]

Of the signaling molecules reported to be up-regulated in chronic hypertension, p38MAPK phosphorylation was decreased in SHR as a result of dietary intervention with lentils. Vledt et al[35] previously reported that decreased p38MAPK activation is related to decreased NADPH oxidase (Nox) activity. Nox, which is up-regulated in the SHR in response to hypertension and oxidative stress,[36] is a cellular source of superoxide radicals.[37] Since p38MAPK is redox sensitive, its down-regulation may pertain to the antioxidant capacity of lentils.[38] Decreased p38MAPK activity relates well to the changes in vascular function that occurred with the lentil diets, since restoring arterial compliance and reducing remodeling is an important aspect of disease management and has been suggested as a marker of intervention effectiveness.[5]

Of the lentil varieties tested, the green lentil-based diet was able to restore vascular compliance in SHR to a level better than the normotensive WKY control group. Mixed lentils also decreased stiffness in WKY animals. In the case of the green lentil-fed SHR, improved compliance independent of a reduction in BP can be explained by less arterial remodeling due to the decrease in activated p38MAPK. These results underscore the fact that changes in BP, vascular remodeling, and vascular compliance are not Inextricably linked.

Lentils contain a variety of nutrients and bioactive compounds. The reduction in LDL-C across all lentil-fed groups was likely a reflection of the equivalence in soluble fibre in the lentil diets. Thus, LDL-C does not explain the changes in arterial function that were obtained. On the other hand, it may be that other bioactive compounds present in lentils, particularly polyphenols, may be responsible for promoting positive vascular remodeling and Increased compliance in lentil-fed SHR. If lentils are able to abrogate vascular remodeling regardless of BP status, this could make them valuable adjuncts to pharmaceutical therapy by decreasing dosage or multiple drug therapy for control of hypertension-induced comorbidities. Lentils could also be a component of vascular disease prevention, since pulses are an Inexpensive, nutrient dense food source that can be incorporated Into to the typical Western diet in various ways, including as a supplement.

The invention will now be further elucidated by way of example; however, the invention is not necessarily limited to the examples.

EXAMPLES

Results

Blood Pressure and Pulse Wave Velocity

SHR animals had higher diastolic blood pressure (DBP), systolic blood pressure (SBP) and mean arterial pressure (MAP) than normotensive WKY animals at baseline and Week 8 (FIG. 1), but there were no differences due to diet. Likewise, SHR animals had consistently higher peak velocity, mean flow velocity, and minimum flow velocity than the WKY, while pulsatile (relation between peak and minimum flow rates) and resistivity (downstream contribution to arterial resistance) indices were lower in SHR than WKY, but overall there were no significant dietary effects on these PWV parameters (Table 3).

Vascular Properties

Myography was employed to investigate various vascular parameters. Wall thickness and lumen diameter readings taken at 45 mmHg indicated that the SHR-Ctrl had a smaller external diameter (FIG. 2A) and a smaller lumen diameter (FIG. 2B) than WKY-Ctrl. Feeding SHR green or red lentils, but not mixed lentils, restored external and lumen diameters to values not statistically different from WKY-Ctrl. There were no differences with respect to media width (FIG. 2C) or media cross-sectional area among any of the groups. SHR-Ctrl had higher M:L ratios (+93%) than the WKY-Ctrl (FIG. 2D). WKY-ML had a higher M:L ratio (+45%) compared to WKY-Ctrl. SHR-ML and SHR-GL had decreased M:L ratios (−22% and −21%, respectively) compared to SHR-Ctrl. Although SHR-RL had a similar reduction in the M:L ratio (−17%) compared to SHR-Ctrl.

Figure 3:
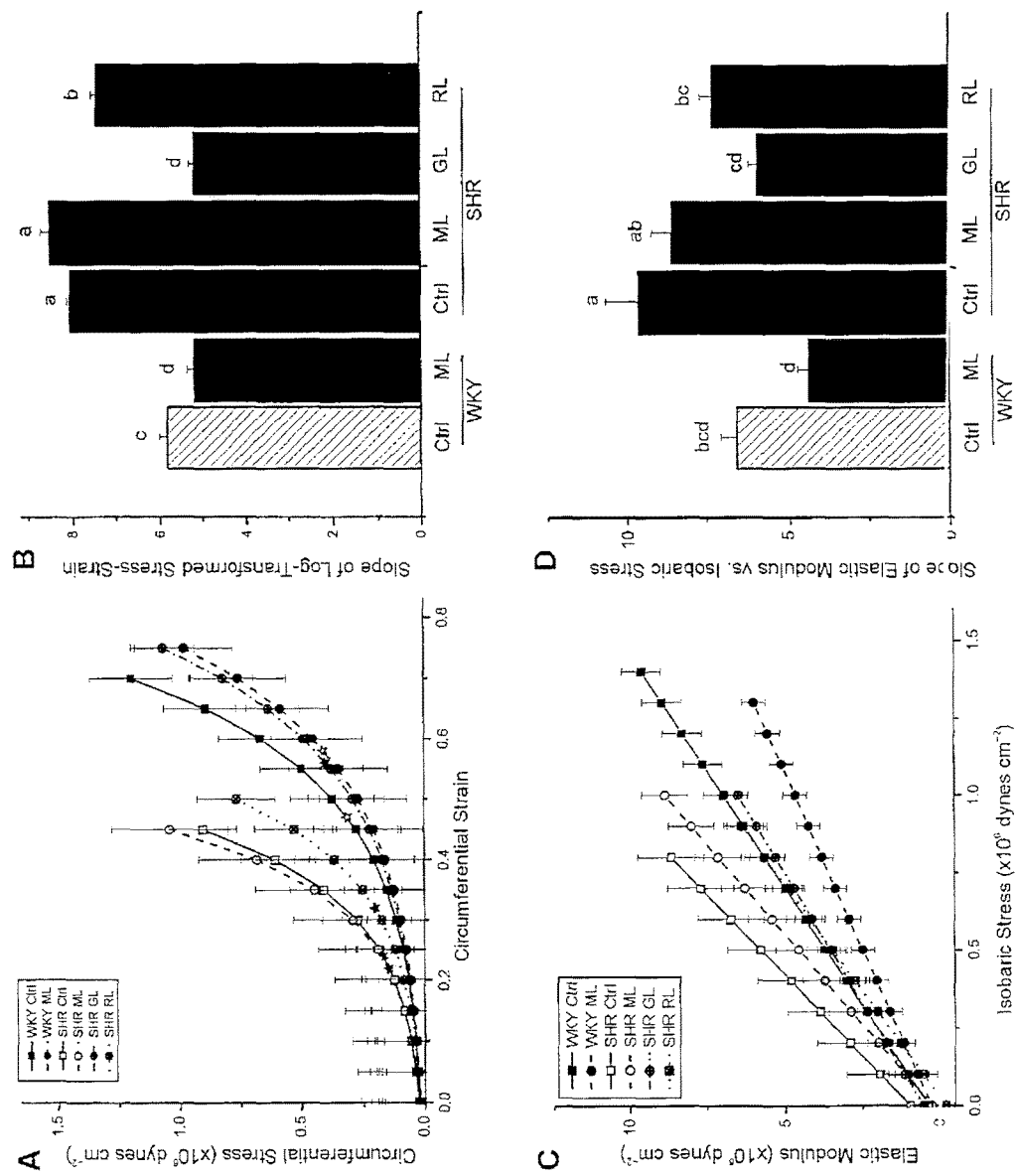
FIG. 3. Isobaric measurements obtained from the pressure myograph. A) Stress-strain relationship, B) Slope of log-transformed stress-strain relationship to determine vascular compliance, the ability of arteries to stretch in response to increased pressure, C) Elastic modulus versus isobaric stress, and D) Slope of elastic modulus versus isobaric stress, a measurement of arterial stiffness. In A) the stars (★) on the graph represent the point when the change in slope becomes ≥100 000 dynes/cm$^2$, an arbitrary 'break point'. Data are expressed as means±SE (n=6-7/group). Bars with different letters are significantly different ($P<0.05$).

The stress-strain curve showed that the SHR-Ctrl animals had impaired ability to mitigate the tension caused by increased arterial pressure compared to WKY-Ctrl, indicating decreased arterial compliance in the SHR model (FIG. 3A). The SHR-ML group showed no improvement compared to the SHR-Ctrl. The SHR-RL curve fell between the SHR-Ctrl and WKY-Ctrl. The SHR-GL curve fell to the right of the WKY-Ctrl curve indicating complete restoration of the vessel's ability to buffer pressure changes on the stress strain curve. The curve for the WKY-ML group was to the right of the WKY-Ctrl curve suggesting a further improvement in vessel properties in the normotensive model. The slopes of the log-transformed stress-strain relationship also indicated that WKY-ML had improved arterial compliance compared to WKY-Ctrl (FIG. 3B). Furthermore, both SHR-RL and SHR-GL, but not SHR-ML, had improved arterial compliance compared to SHR-Ctrl; however, the magnitude of effect was greater with green lentils such that the value for the SHR-GL group was not different from the normotensive WKY-ML animals.

The stiffness of the vessel wall components (I.e. Independent of vascular geometry) is mathematically reflected as the slope of the elastic modulus versus isobaric stress. Wall component stiffness was increased in the SHR-Ctrl (÷46%) compared to the WKY-Ctrl animals (FIG. 3C, D). The SHR-GL and SHR-RL had decreased stiffness (~38% and ~24%, respectively) compared to SHR-Ctrl, with no significant difference between SHR-Ctrl and SHR-ML WKY-ML had decreased arterial stiffness (~34%) compared to WKY-Ctrl. The changes seen in arterial wall component stiffness assessed by the slope of the elastic modulus versus isobaric stress (FIG. 3D) reflected similar changes seen in arterial stiffness assessed by the slope of the log-transformed stress-strain relationship (FIG. 3B).

To account for the altered physical properties of the vessels, two distinct analyses were performed. First, cell number and cell size in the media were quantified to determine whether these factors were related to wall thickness. There was no difference in cell number between WKY and SHR, nor between SHR-Ctrl and SHR lentil-fed groups (Table 1). In contrast, cell size was significantly larger (by 56%) in SHR relative to WKY (Table 1). Second, image analysis was used to provide the relative content of elastin and collagen in the vessels. Again, no differences were observed (Table 1). Interestingly, although the amount of non-collagen/non-elastin stained extracellular matrix (nsECM) in the vessel wall of SHR was not statistically different from that of WKY, the ratio of collagen to nsECM shows a trend towards greater amounts of nsECM at the expense of collagen (Table 1). The reverse is seen in comparing the SHR-Ctrl group with the SHR group fed green lentils (Table 1). These data indicate that the nsECM component(s) is responsible for the increased wall thickness in hypertensive animals, and is decreased as a result of green lentil consumption.

Protein Levels

Figure 4:
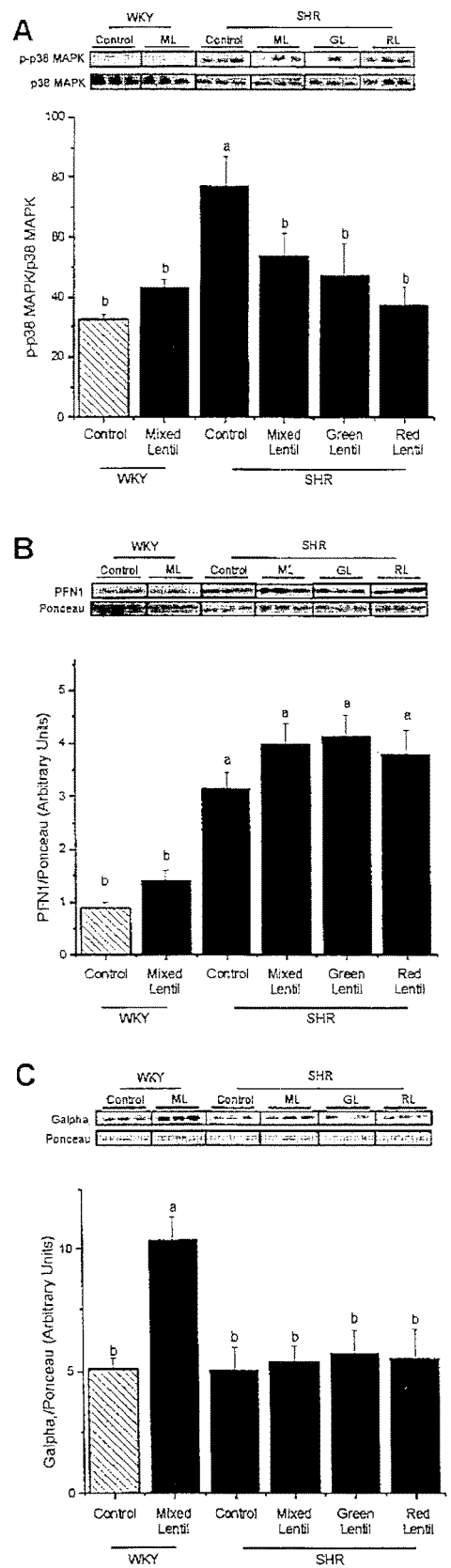
FIG. 4. Quantification of protein levels in aorta. Aorta protein samples were analyzed by Western blotting with primary antibodies to A) phospho-p38MAPK$^{T180/Y182}$ and p38MAPK, B) profilin-1 (PFN1) and C) Galpha$_i$ (G$\alpha_{(i)}$). The antibodies were applied at a concentration of 1:1000 and incubated from 1 h to overnight. Rabbit secondary antibody was applied at a concentration of 1:10,000 and incubated for 1 h. Ponceau stained membranes were scanned then analyzed on AlphaView and "Blue background average" was selected. Data are expressed as mean±SE (n=7-10/group). Bars with different letters are significantly different ($P<0.05$).

Phosphorylated p38MAPK$^{T180/Y182}$ was increased in the SHR-Ctrl versus WKY, but returned to the level of normotensive WKY in SHR lentil-fed animals when normalized to p38MAPK (FIG. 4A). There were no differences among groups with respect to p-ERK1/2 when normalized to ERK1/2. SHR animals had higher PFN-1 levels than WKY, with no dietary differences detected (FIG. 4B). There were also no differences between WKY and SHR animals with respect to Gαi levels, although Gαl levels were increased in WKY-ML compared to the other groups (FIG. 4C).

Tissue Weights and Body Composition

Genotype differences between SHR and WKY were observed for body and organ weights, and body composition, but no differences due to diet were seen (Tables 4, 5).

Tissue Weights and Body Composition

Differences between SHR and WKY were observed for body weight and organ weights, including the heart, as well as body composition, thus indicating a genotype effect, but no differences were seen as a result of the diets (Tables 4, 5).

Serum Biochemistry

Figure 5:
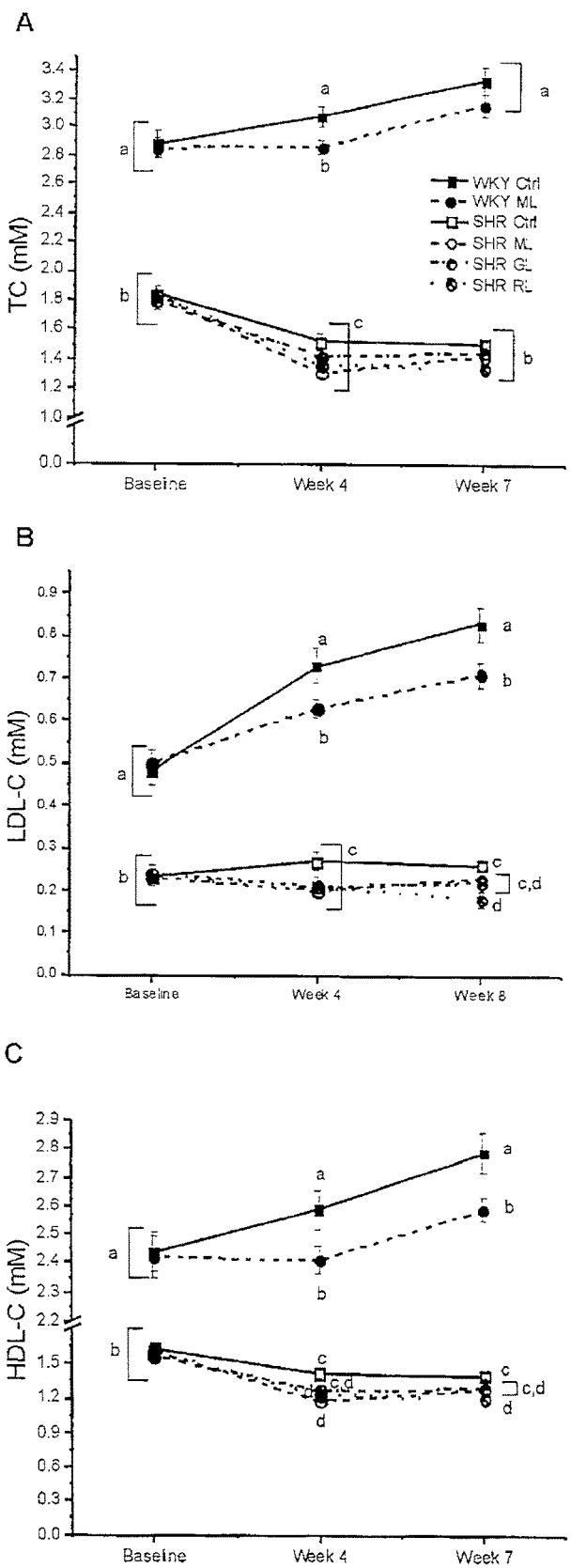
FIG. 5: Serum biochemistry. A) Total cholesterol (TC), B) LDL-C, and C) HDL-C were measured in serum samples obtained after a 12-hour fast using a Cobas C111 auto analyzer. Data are expressed as means±SE (n=8-10/group). The legend inset in panel A applies to all panels. At each time point, different letters represent significant differences ($P<0.05$).

At baseline, week 4, and week 7, WKY animals had higher TC, LDL-C, and HDL-C compared to all SHR groups. WKY-ML had 7% lower TC than WKY-Ctrl at week 4 but there were no differences among SHR groups with respect to TC at any time point (FIG. 5). At week 7, WKY-ML had 7% and 14% lower LDL-C and HDL-C, respectively, compared to WKY-Ctrl. Also at week 7, LDL-C and HDL-C were 31% and 14% lower, respectively, in SHR-RL and 15% and 9% lower, respectively, in SHR-GL compared to SHR-Ctrl. No dietary effects were observed except for reductions in LDL-C and HDL-C with WKY-ML relative to WKY Ctrl and SHR-RL versus SHR-Ctrl (FIG. 5). At all time points, WKY animals had higher serum TG and glucose and lower serum urea levels than SHR with no effect due to dietary intervention. There were no differences among groups with respect to serum creatinine. This demonstrates that LDL-C lowering also occurs in 'healthy' animals as well as those that are hypertensive.

Preparation of Lentil Hull Extract

Lentil extract was prepared by mixing ground lentil hulls with methanol (5 vol methanol:1 vol powder) at room temperature for 1 hour, at which time the powder was pelleted by centrifugation and the supernatant transferred to a new tube for storage at −20° C. until testing occurred.

Figure 6:
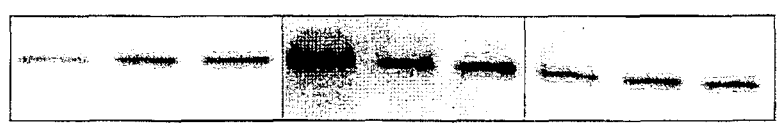
FIG. 6: Inhibition of p38MAPK activation by the Lentil extract. Quiescent smooth muscle cells were treated for 15 min with 50 nM insulin-like growth factor-1 (IGF-1) with or without prior exposure to 2 μL lentil hull methanol extract for 30 min. The cells were subsequently lysed and analyzed by Western blotting for phospho-p38MAPK. Representative bands are shown in (a), while densitometric quantification is shown in (b). The data are presented as mean±SEM. *, significant increase over untreated control; #, significant change from IGF-1 treated cells.
Figure 6:
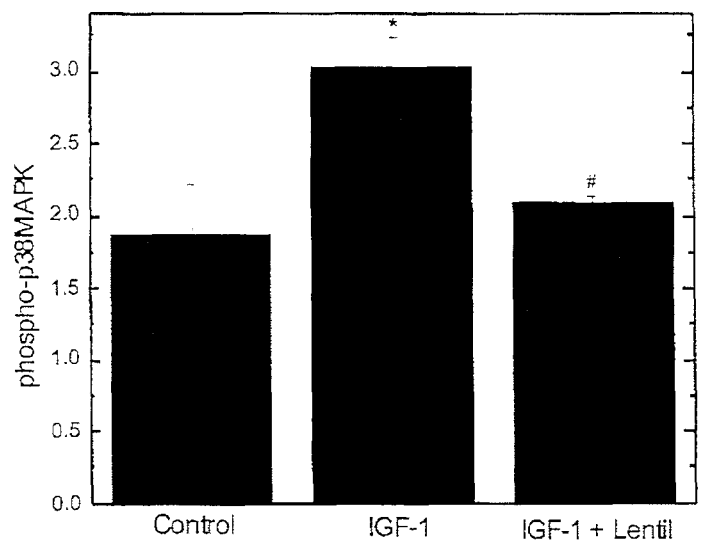

FIG. 6 demonstrates the ability of the hull extract to prevent activation of a key cellular element in the development of arterial stiffness. This demonstrates that addition of an extract made from lentils is capable of blocking the activation of p38 MAP kinase, which occurs when vessels are stressed by conditions such as hypertension that lead to arterial remodeling. Methodology for preparation of the cells, and how experiments using these cells are run is described in Molnar et al (J Cell Commun Signal 8:29-37, 2014).

Materials and Methods

Animals

Seventeen-week-old SHR and WKY rats (Charles River Laboratories, Saint-Constant, QC, Canada) were randomly assigned to a study group (n=10/group) for the 8-week intervention period: SHR control (SHR-Ctrl), SHR mixed lentil (SHR-ML), SHR green lentil (SHR-GL), SHR red lentil (SHR-RL), WKY control (WKY-Ctrl), and WKY mixed lentil (WKY-ML).

Experimental Diets

Diets were formulated and prepared as previously described.[18] Whole lentils were cooked, freeze-dried and powdered before addition to the diets to inactivate anti-nutritional factors and mimic preparation for human consumption. The dose (30% w/w lentils) was based on our previous study[18] and the work of others[39] demonstrating positive biological effects without changes in body weight.

Blood Pressure

BP was measured at baseline and week 8 by tail-cuff plethysmography (CODA™ system, Kent Scientific, Torrington, Conn., USA). Only animals giving five or more measurements per BP cycle were used in calculating systolic blood pressure (SBP), diastolic blood pressure (DBP) and mean arterial pressure (MAP) averages.

Pulse Wave Velocity

Pulse wave velocity (PWV) in the femoral artery was measured in anesthetized rats with a 10-MHz ECG-triggered Doppler probe (Indus instruments, Houston, Tex., USA). The PWV analysis was done in a blinded manner using the Doppler Signal Processing Workstation program (DSPW Version 1.624, Indus instruments, Houston, Tex., USA) as previously described.[18] The software was used to locate the baseline of the PWV trace as well as determine the pulse waveforms on the EGC trace. Afterwards, the peak velocity (PV), the mean flow velocity (MeFV), the minimum flow velocity (MFV), the pulsatile index (PI) and the resistivity index (RI) were manually identified on the Doppler trace. Approximately 17 peaks were analyzed per trace, with three traces per animal per time point (baseline and week 7).

Body Composition

Body composition (fat mass, lean body mass, total and free water) was assessed in vivo through use of an EchoMRI-700™ whole body Quantitative Magnetic Resonance (QMR) instrument (EchoMRI, Houston, Tex., USA) at baseline, week 4, and week 7.

Tissue Collection

Rats were euthanized by injecting an overdose of pentobarbital. The heart, liver, per-renal and epididymal adipose tissues were excised and weighed to determine organ to body weight ratios. The left ventricle was isolated from the rest of the heart and weighed. The aorta was excised and a portion of descending aorta was embedded in optimal cutting temperature (OCT) compound (Sakura Finetek, Torrance, Calif., USA) and frozen in a dry ice-ethanol bath, while the remainder of the aorta was snap frozen in liquid nitrogen and stored at $-80°$ C.

Pressure Myography

A third order vessel isolated from the first 10 cm of mesenteric fat was mounted on a pressure myograph (Living Systems Instrumentation, Burlington, Vt., USA), pressurized to 45 mmHg, allowed to equilibrate for one hour in Krebs-Henseleit (KH) buffer (25 mM $NaHCO_3$, 5.5 mM glucose, 2.7 µM NaEDTA, 120 mM NaCl, 4.7 mM KCl, 1.2 mM $MgSO_4$, 1.2 mM $KH_2PO_4$, 2.5 mM $CaCl_2$, pH7.4) at $37°$ C., then challenged with 125 mM KCl solution (in KH buffer) to constrict and check artery viability. After the 30 minutes in $Ca^{2+}$-free KH buffer containing 10 mM EGTA for 30 minutes, triplicate measurements of lumen diameter and left and right wall thickness were made at 3, 10, 20, 30, 40, 60, 80, 100, 120, and 140 mmHg. Calculations of stiffness of the artery media stress, media strain, elastic modulus, and media cross-sectional area, were done as described previously.[4,26]

Aorta Histology

Sections were prepared and fixed as described previously.[18] Elastin and collagen were differentially stained with an Elastin Stain Kit (Sigma-Aldrich, St Louis, Mo., USA), and digital images were analyzed with ImagePro Plus (Media Cybernetics, Rockville, Md., USA) to obtain lumen diameter, media thickness, M:L ratio, media cross-sectional area and external diameter.[18] The sections were also analyzed with ImageJ software[27] to determine the relative elastin (black), collagen (red) and other (yellow) components of the vessels. Sections stained with Lee's methylene blue[28] were used to quantify cell number per unit area.[27]

Western Blotting

Aorta lysates were prepared and immunoblots were analyzed with primary antibodies (Giα, p38MAPK, phospho-p38MAPK Thr-180/Tyr-182, PFN1, ERK1/2, phospho-ERK1/2) from Cell Signaling (Danvers, Mass., USA) as previously described.[29]

Serum Biochemistry

Fasting serum samples obtained at baseline (week 0), week 4, and week 7 from the saphenous vein were analyzed with a Cobas C111 auto analyzer (Roche Diagnostics, Indianapolis, Ind., USA) for total cholesterol (TC), high-density lipoprotein cholesterol (HDL-C), low-density lipoprotein cholesterol (LDL-C), triglycerides (TG), glucose, creatinine and urea.

The scope of the claims should not be limited by the preferred embodiments set forth in the examples, but should be given the broadest interpretation consistent with the description as a whole.

REFERENCES

1. Bromfield S, Muntner P. High blood pressure: The leading global burden of disease risk factor and the need for worldwide prevention programs. *Curr Hypertens Rep.* 2013; 15:134-136.
2. Nguyen T, Lau D C. The obesity epidemic and its impact on hypertension. *Can J Cardiol.* 2012; 28:326-333.
3. Sun Z. Aging, arterial stiffness, and hypertension. *Hypertension.* 2015; 65:252-256.
4. Park J B, Schiffrin E L. Small artery remodeling is the most prevalent (earliest?) form of target organ damage in mild essential hypertension. *J Hypertens.* 2001; 19:921-930.
5. Rizzoni D, Agabiti-Rosel E. Structural abnormalities of small resistance arteries in essential hypertension. *Intern Emerg Med.* 2012; 7:205-212.
6. Intengan H D, Schiffrin E L. Vascular remodeling in hypertension: roles of apoptosis, inflammation, and fibrosis. *Hypertension.* 2001; 38:581-587.
7. Gunduz F, Baskurt O K, Meiselman H J. Vascular dilation responses of rat small mesenteric arteries at high intravascular pressure in spontaneously hypertensive rats. *Circ J.* 2009; 73:2091-2097.
8. Luft F C. Molecular mechanisms of arterial stiffness: new insights. *J Am Soc Hypertens.* 2012; 6:436-438.
9. Oparil S, Zaman M A, Calhoun D A. Pathogenesis of hypertension. *Ann Intern Med.* 2003; 139:761-776.
10. Eftekhari A, Mathiassen O N, Buus N H, Gotzsche O, Mulvany M J, Christensen K L. Changes in blood pressure and systemic vascular resistance do not predict microvascular structure during treatment of mild essential hypertension. *J Hypertens.* 2012; 30:794-801.
11. Cushman W C. The burden of uncontrolled hypertension: morbidity and mortality associated with disease progression. *J Clin Hypertens (Greenwich).* 2003; 5:14-22.
12. Rimm E B, Ascherio A, Giovannucci E, Spiegelman D, Stampfer M J, Wilett W C. Vegetable, fruit, and cereal fiber intake and risk of coronary heart disease among men. *JAMA.* 1996; 275:447-451.
13. Bazzano L A, He J, Ogden L G, Lorla C, Vupputuri S, Myers L, Whelton P K. Legume consumption and risk of coronary heart disease in US men and women: NHANES I Epidemiologic Follow-up Study. *Arch Intern Med.* 2001; 161:2573-2578.
14. Boye J I, Roufik S, Pesta N, Barbana C. Anglotensin I-converting enzyme inhibitory properties and SDS-PAGE or red lentil protein hydrolysates. *LWT—Food Science and Technology.* 2010; 43:987-991.
15. Yao F, Sun C, Chang S K. Lentil polyphenol extract prevents anglotensin II-induced hypertension, vascular remodelling and perivascular fibrosis. *Food Funct* 2012; 3:127-133.
16. Zahradka P, Wright B, Weighel W, Blewett H, Baldwin A, O K, Guzman R P, Taylor C G. Daily non-soy legume consumption reverses vascular impairment due to peripheral artery disease. *Atherosclerosis.* 2013; 230:310-314.
17. Perez-Vizcaino F, Bishop-Bailley D, Lodi F, Duarte J, Cogolludo A, Moreno L, Bosca L, Mitchell J A, Warner T D. The flavonoid quercetin induces apoptosis and inhibits JNK activation in intimal vascular smooth muscle cells. *Biochem Biophys Res Commun.* 2006; 346:919-925.
18. Hanson M G, Zahradka P, Taylor C G. Lentil-based diets attenuate hypertension and large-artery remodelling in spontaneously hypertensive rats. *Br J Nutr.* 2014; 111: 690-698.
19. Barbana C, Boye J I. Angiotensin I-converting enzyme inhibitory properties of lentil protein hydrolysates: Determination of the kinetics of inhibition. *Food Chemistry.* 2011; 127:94-101.
20. Doggrell S A, Brown L. Rat models of hypertension, cardiac hypertrophy and failure. *Cardiovasc Res.* 1998; 39:89-105.
21. Gao Y J, Yang L F, Stead S, Lee R M. Flow-induced vascular remodeling in the mesenteric artery of spontaneously hypertensive rats. *Can J Physiol Pharmacol.* 2008; 86:737-744.
22. Cheng J F, Ni G H, Chen M F, Li Y J, Wang Y J, Wang C L, Yuan Q, Shi R Z, Hu C P, Yang T L involvement of profiln-1 In angiotensin II-induced vascular smooth muscle cell proliferation. *Vascul Pharmacol.* 2011; 55:34-41.
23. Otsuka S, Sugano M, Makino N, Sawada S, Hata T, Niho Y. Interaction of mRNAs for anglotensin II type 1 and type 2 receptors to vascular remodeling in spontaneously hypertensive rats. *Hypertenskin.* 1998; 32:467-472.
24. Jing L, Zhang J Z, Zhao L, Wang Y L, Guo F Y. High-expression of transforming growth factor beta1 and phosphorylation of extracellular signal-regulated protein kinase in vascular smooth muscle cells from aorta and renal arterioles of spontaneous hypertension rats. *Clin Exp Hypertens.* 2007; 29:107-117.
25. Wang Y, Zhang J, Gao H, Zhao S, Ji X, Liu X, You B, Li X, Qiu J. Profilin-1 promotes the development of hypertension-induced artery remodeling. *J Histochem Cytochem.* 2014; 62:298-310.
26. Behbahani J, Thandaply S J, Louis X L, Huang Y, Shao Z, Kopilas M A, Wojclechowski P, Netticadan T, Anderson H D. Resveratrol and small artery compliance and remodeling in the spontaneously hypertensive rat. *Am J Hypertens.* 2010; 23:1273-1278.
27. Schneider C A, Rasband W S, Eliceiri K W. NIH Image to ImageJ: 25 years of Image analysis. *Nat Methods.* 2012; 9:671-675.
28. Wilson D P, Saward L, Zahradka P, Cheung P K. Angiotensin II receptor antagonists prevent neointimal proliferation in a porcine coronary artery organ culture model. *Cardovasc Res.* 1999; 42:761-772.
29. Yau L, Lukes H, McDiarmid H, Werner J, Zahradka P. Insulin-like growth factor-I (IGF-I)-dependent activation of pp42/44 mitogen-activated protein kinase occurs independently of IGF-I receptor kinase activation and IRS-1 tyrosine phosphorylation. *Eur J Biochem.* 1999; 266: 1147-1157.
30. Zhang L, Li Y, Chen M, Su X, YI D, Lu P, Zhu D. 15-LO/15-HETE mediated vascular adventitla fibrosis via p38 MAPK-dependent TGF-beta. *J Cell Physiol.* 2014; 229:245-257.
31. Muslin A J. MAPK signalling in cardiovascular health and disease: molecular mechanisms and therapeutic targets. *Clin Sci (Lond).* 2008; 115:203-218.
32. Osman N, Ballinger M L, Dadlani H M, Getachew R, Burch M L, Little P J. p38 MAP kinase mediated proteoglycan synthesis as a target for the prevention of atherosclerosis. *Cardiovasc Hematol Disord Drug Targets.* 2008; 8:287-292.
33. Dodd T, Jadhav R, Wiggins L, Stewart J, Smith E, Russell J C, Rocic P. MMPs 2 and 9 are essential for coronary collateral growth and are prominently regulated by p38 MAPK. *J Mol Cell Cardiol.* 2011; 51:1015-1025.
34. Amaral S L, Michellni LC. Effect of gender on training-induced vascular remodeling in SHR. *Braz J Med Biol Res.* 2011; 44:814-826.
35. Viedt C, Soto U, Krleger-Brauer H I, Fei J, Elsing C, Kubler W, Kreuzer J. Differential activation of mitogen-activated protein kinases in smooth muscle cells by anglotensin II: involvement of p22phox and reactive oxygen species. *Arterloscer Thromb Vasc Biol.* 2000; 20:940-948.
36. Lassegue B, Sorescu D, Szocs K, Yin Q, Akers M, Zhang Y, Grant S L, Lambeth J D, Griendling K K. Novel gp91(phox) homologues in vascular smooth muscle cells: nox1 mediates anglotensin II-induced superoxide formation and redox-sensitive signaling pathways. *Circ Res.* 2001; 88:888-894.
37. Sanchez M, Gallsteo M, Vera R, Vilar I C, Zarzuelo A, Tamargo J, Perez-Vizcaino F, Duarte J. Quercetin down-regulates NADPH oxidase, increases eNOS activity and prevents endothelial dysfunction in spontaneously hypertensive rats. *J Hypertens.* 2006; 24:75-84.
38. Amarowicz R, Estrella I, Hernandez T. Free radical-scavenging capacity, antioxidant activity, and phenolic composition of green lentil (*Lens culinaris*). *Food Chemistry.* 2010; 121:705-711.
39. Thompson M D, Thompson H J, Brick M A, McGinley J N, Jiang W, Zhu Z, Wolfe P. Mechanisms associated with dose-dependent inhibition of rat mammary carcinogenesis by dry bean (*Phaseolus vulgaris*, L). *J Nutr.* 2008; 138:2091-2097.
40. Avolio A, Jones D, Tafazzoli-Shadpour M (1998) Quantification of alterations in structure and function of elastin in the arterial media. Hypertension 32:170-175
41. Lakatta E G, Mitchell J H, Pomerance A, Rowe G G (1987) Human aging: Changes in structure and function. J Am Coil Cardiol 10:42A-47A
42. Smith E R, Tomlinson L A, Ford M L, McMahon L P, Rajkumar C, Holt S G (2012) Elastin degradation is associated with progressive aortic stiffening and all-cause mortality in predialysis chronic kidney disease. Hypertension 59:973-978
43. Chung C M, Lin Y S, Chu C M, Chang S T, Cheng H W, Yang T Y, Hsiao J F, Pan K L, Hsu J T (2012) Arterial stiffness is the independent factor of left ventricular hypertrophy determined by electrocardiogram. Am J Med Sci 344:190-193

44. Kaess B M, Rong J, Larson M G, Hamburg N M, Vita J A, Levy D, Benjamin E J, Vasan R S, Mitchell G F (2012) Aortic stiffness, blood pressure progression, and incident hypertension. JAMA 308:875-881
45. McVeigh G E, Bratteli C W, Morgan D J, Allnder C M, Glasser S P, Finkelstein S M, Cohn J N (1999) Age-related abnormalities in arterial compliance identified by pressure pulse contour analysis: Aging and arterial compliance. Hypertension 33:1392-1398
46. Mitchell G F, Guo C Y, Benjamin E J, Larson M G, Keyes M J, Vita J A, Vasan R S, Levy D (2007) Cross-sectional correlates of increased aortic stiffness in the community: The framingham heart study. Circulation 115:2628-2636
47. Sutton-Tyrrell K, Newman A, Simonsick E M, Havilk R, Pahor M, Lakatta E, Spurgeon H, Vaitkevicius P (2001) Aortic stiffness is associated with visceral adiposity in older adults enrolled in the study of health, aging, and body composition. Hypertension 38:429-433
48. Roman M J, Devereux R B, Kizer J R, Lee E T, Galloway J M, All T, Umans J G, Howard B V (2007) Central pressure more strongly relates to vascular disease and outcome than does brachial pressure: The strong heart study. Hypertension 50:197-203.
49. Saphirstein R J, Morgan K G (2014) The contribution of vascular smooth muscle to aortic stiffness across length scales. Microcirculation 21:201-207
50. Chirinos J A (2012) Arterial stiffness: Basic concepts and measurement techniques. J Cardiovasc Transl Res 5:243-255
51. Laurent S, Cockcroft J, Van Bortel L, Boutouyrle P, Glannattasio C, Hayoz D, Pannier B, Vlachopoulos C, Wilkinson I, Struijker-Boudler H (2006) Expert consensus document on arterial stiffness: Methodological issues and clinical applications. Eur Heart J 27:2588-2605
52. Oliver J J, Webb D J (2003) Noninvasive assessment of arterial stiffness and risk of atherosclerotic events. Arterioscler Thromb Vasc Biol 23:554-566
53. O'Rourke M F, Staessen J A, Vlachopoulos C, Duprez D, Plante G E (2002) Clinical applications of arterial stiffness; definitions and reference values. Am J Hypertens 15:426-444
54. Reference Values for Arterial Stiffness' Collaboration (2010) Determinants of pulse wave velocity in healthy people and in the presence of cardiovascular risk factors: 'Establishing normal and reference values'. Eur Heart J 31:2338-2350
55. Duprez D A, Cohn J N (2007) Arterial stiffness as a risk factor for coronary atherosclerosis. Curr Atheroscler Rep 9:139-144
56. Shokawa T, Imazu M, Yamamoto H, Toyofuku M, Tasaki N, Okimoto T, Yamane K, Kohno N (2005) Pulse wave velocity predicts cardiovascular mortality: Findings from the hawaii-los angeles-hiroshima study. Circ J 69:259-264
57. Williams B, Lacy P S, Thornm S M, Cruickshank K, Stanton A, Collier D, Hughes A D, Thurston H, O'Rourke M, CAFE investigators, Anglo-Scandinavian Cardiac Outcomes Trial Investigators, CAFE Steering Committee and Writing Committee (2006) Differential impact of blood pressure-lowering drugs on central aortic pressure and clinical outcomes: Principal results of the conduit artery function evaluation (CAFE) study. Circulation 113:1213-1225
58. Willum-Hansen T, Staessen J A, Torp-Pedersen C, Rasmussen S, Thijs L, Ibsen H, Jeppesen J (2006) Prognostic value of aortic pulse wave velocity as index of arterial stiffness in the general population. Circulation 113:664-670
59. Corretti M C, Anderson T J, Benjamin E J, Celermajer D, Charbonneau F, Creager M A, Deanfield J, Drexler H, Gerhard-Herman M, Herrington D, Valiance P, Vita J, Vogel R, International Brachial Artery Reactivity Task Force (2002) Guidelines for the ultrasound assessment of endothelial-dependent flow-mediated vasodilation of the brachial artery: A report of the international brachial artery reactivity task force. J Am Coil Cardiol 39:257-265

TABLE 1

Aorta Morphology[†]

| Parameter | WKY Control | SHR Control | SHR Green Lentil |
|---|---|---|---|
| Cell Number/Section | 812 ± 60 | 880 ± 28 | 932 ± 60 |
| Cell Size (µm$^2$) | 231 ± 5[b] | 360 ± 30[a] | 385 ± 25[a] |
| Elastin (pixels) | 50.5 ± 2.4 | 47.4 ± 5.9 | 46.5 ± 2.0 |
| Collagen (pixels) | 16.8 ± 4.0 | 11.1 ± 4.7 | 12.9 ± 4.8 |
| nsECM (pixels) | 5.55 ± 2.4 | 10.2 ± 2.1 | 5.76 ± 3.6 |
| Collagen/(Collagen + nsECM) | 0.800 ± 0.052 | 0.477 ± 0.119 | 0.614 ± 0.065 |

[†]Sections stained to visualize the vascular smooth muscle cells (Lee's methylene blue) and elastin and collagen (Elastin Stain Kit) were analyzed as described in the Methods. Data are expressed as means ± SE (n = 5/group). Within a row, different superscript letters represent significant differences (P ≤ 0.05) and an absence of letters indicates no statistical differences.
Abbreviations:
nsECM, non-collagen/non-elastin stained extracellular matrix.

TABLE 2

Diet Formulations.

| | AIN-93G Control | Mixed Lentil | Green Lentil | Red Lentil |
|---|---|---|---|---|
| A - Ingredients[a] | | g/kg | | |
| Casein | 200 | 113 | 113 | 113 |
| Cornstarch | 397 | 229.5 | 229.5 | 229.5 |
| Maltodextrin | 132 | 132 | 132 | 132 |
| Sucrose | 100 | 100 | 100 | 100 |
| Cellulose | 50 | 5 | 5 | 5 |
| L-cysteine | 3 | 3 | 3 | 3 |
| Choline Bitartrate | 2.5 | 2.5 | 2.5 | 2.5 |
| Mineral Mix[b] | 35 | 35 | 35 | 35 |
| Vitamin Mix[c] | 10 | 10 | 10 | 10 |
| Soybean Oil[d] | 70 | 70 | 70 | 70 |
| Pulse Powder[e] | | | | |
| Green Lentil | — | 150 | 300 | — |
| Red Lentil | — | 150 | — | 300 |
| Total (g) | 1000 | 1000 | 1000 | 1000 |
| B - Proximate Analysis[f] | | % | | |
| Moisture | 7.1 | 4.6 | 4.6 | 7.5 |
| Dry Matter | 93.0 | 95.4 | 95.4 | 92.5 |
| Crude Protein | 19.2 | 17.2 | 17.3 | 17.3 |
| Crude fibre | 1.4 | 1.4 | 1.4 | 1.3 |
| Fat | 7.2 | 7.5 | 7.3 | 7.1 |
| Ash | 2.3 | 3.0 | 2.8 | 2.8 |

[a]Dyets Inc., Bethlehem, PA, USA, except pulse powders
[b]AIN-93G MX
[c]AIN-93 VX
[d]With 0.02% TBHQ - tert-butylhydroquinone
[e]Pulse powder prepared as described in Hanson et al[18]
[f]Central Testing Labs Ltd., Winnipeg, MB, Canada

TABLE 3

Pulse wave velocity measurements.[†]

|  |  | WKY | | SHR | | | |
|---|---|---|---|---|---|---|---|
|  |  | Control | Mixed Lentil | Control | Mixed Lentil | Green Lentil | Red Lentil |
| PV (cm/s) | Baseline | 29 ± 0.7[b] | 29 ± 1.0[b] | 36 ± 0.5[a] | 35 ± 1.2[a] | 36 ± 0.8[a] | 36 ± 1.1[a] |
|  | Week 8 | 31 ± 1.5[b] | 32 ± 1.1[b] | 36 ± 1.1[a] | 35 ± 0.4[a] | 37 ± 0.7[a] | 35 ± 0.6[a] |
| MeFV (cm/s) | Baseline | 9.9 ± 0.6[b] | 7.5 ± 0.4[b] | 12.1 ± 0.6[a] | 14.4 ± 0.6[a] | 14 ± 0.6[a] | 14.3 ± 0.7[a] |
|  | Week 8 | 10.0 ± 0.5[b] | 8.4 ± 0.4[b] | 13.3 ± 0.6[a] | 15.0 ± 0.5[a] | 14.5 ± 0.5[a] | 14.1 ± 0.6[a] |
| MFV (cm/s) | Baseline | 3.8 ± 0.4[b] | 2.2 ± 0.2[b] | 5.5 ± 0.7[a] | 6.9 ± 0.7[a] | 6.6 ± 0.7[a] | 7.0 ± 0.7[a] |
|  | Week 8 | 3.7 ± 0.4[b] | 2.4 ± 0.2[b] | 6.6 ± 0.7[a] | 8.2 ± 0.6[a] | 7.5 ± 0.6[a] | 7.2 ± 0.6[a] |
| PI | Baseline | 3.1 ± 0.2[b] | 3.7 ± 0.2[b] | 2.6 ± 0.2[a] | 2.0 ± 0.1[a] | 2.1 ± 0.1[a] | 2.1 ± 0.1[a] |
|  | Week 8 | 3.0 ± 0.1[b] | 3.6 ± 0.2[b] | 2.4 ± 0.1[a] | 1.9 ± 0.2[a] | 2.0 ± 0.1[a] | 2.1 ± 0.1[a] |
| RI | Baseline | 0.92 ± 0.01[b] | 0.93 ± 0.01[b] | 0.80 ± 0.03[a] | 0.81 ± 0.02[a] | 0.82 ± 0.02[a] | 0.81 ± 0.02[a] |
|  | Week 8 | 0.92 ± 0.01[b] | 0.92 ± 0.01[b] | 0.77 ± 0.03[a] | 0.78 ± 0.02[a] | 0.79 ± 0.01[a] | 0.81 ± 0.02[a] |

[†]Measurements were obtained in vivo in the femoral artery with a 10-MHz ECG-triggered Doppler Probe and analysis was done as described in the Supplementary Methods.
Data are expressed as means ± SE (n = 9-10/group). For means at the same time point, different superscript letters represent significant differences (P ≤ 0.05).
Abbreviations:
PV, peak velocity;
MeFV, mean flow velocity;
MFV, minimum flow velocity;
PI, pulsatile index,
RI, resistivity index.

TABLE 4

Body and Organ Weights.

|  | WKY | | SHR | | | |
|---|---|---|---|---|---|---|
|  | Control | Mixed Lentil | Control | Mixed Lentil | Green Lentil | Red Lentil |
| Initial Body Weight (g) | 322 ± 5[c] | 327 ± 6[bc] | 343 ± 3[a] | 341 ± 5[ab] | 343 ± 4[a] | 337 ± 4[ab] |
| Final Body Weight (g) | 376 ± 7[b] | 398 ± 8[a] | 399 ± 5[a] | 395 ± 8[ab] | 399 ± 5[a] | 384 ± 6[ab] |
| Peri-Renal Adipose (g/100 g BW) | 1.91 ± 0.14[a] | 1.87 ± 0.09[a] | 1.26 ± 0.06[b] | 1.28 ± 0.12[b] | 1.17 ± 0.07[b] | 1.25 ± 0.07[b] |
| Epididymal Adipose (g/100 g BW) | 1.65 ± 0.06[a] | 1.63 ± 0.04[a] | 1.23 ± 0.04[b] | 1.26 ± 0.07[b] | 1.19 ± 0.06[b] | 1.22 ± 0.05[b] |
| Liver (g/100 g BW) | 3.27 ± 0.06[b] | 3.25 ± 0.06[b] | 3.74 ± 0.06[a] | 3.70 ± 0.11[a] | 3.74 ± 0.09[a] | 3.76 ± 0.06[a] |
| Heart Weight (g) | 1.32 ± 0.04[b] | 1.37 ± 0.03[b] | 1.64 ± 0.01[a] | 1.60 ± 0.04[a] | 1.61 ± 0.02[a] | 1.57 ± 0.04[a] |
| (g/100 g BW) | 0.35 ± 0.01[b] | 0.35 ± 0.01[b] | 0.41 ± 0.01[a] | 0.40 ± 0.01[a] | 0.40 ± 0.01[a] | 0.40 ± 0.01[a] |
| Left Ventricle Weight (g) | 0.79 ± 0.02[b] | 0.85 ± 0.02[b] | 1.05 ± 0.04[a] | 1.01 ± 0.05[a] | 1.00 ± 0.03[a] | 1.05 ± 0.03[a] |
| (g/100 g BW) | 0.21 ± 0.01[b] | 0.21 ± 0.01[b] | 0.26 ± 0.01[a] | 0.25 ± 0.01[a] | 0.25 ± 0.01[a] | 0.27 ± 0.01[a] |

Data are expressed as means ± SE (n = 10/group). Within a row, different superscript letters represent significant differences (P ≤ 0.05).
Abbreviations:
BW, body weight.

TABLE 5

Body Composition[†]

|  |  | WKY | | SHR | | | |
|---|---|---|---|---|---|---|---|
|  |  | Control | Mixed Lentil | Control | Mixed Lentil | Green Lentil | Red Lentil |
| Lean Mass (g) | Baseline | 263 ± 4 | 272 ± 3 | 272 ± 2 | 273 ± 2 | 277 ± 2 | 272 ± 2 |
|  | Week 4 | 312 ± 9 | 336 ± 7 | 332 ± 4 | 333 ± 5 | 334 ± 5 | 332 ± 5 |
|  | Week 7 | 336 ± 8 | 351 ± 8 | 360 ± 4 | 354 ± 5 | 359 ± 5 | 342 ± 5 |
| Fat Mass (g) | Baseline | 25 ± 1[b] | 25 ± 2[b] | 35 ± 2[a] | 36 ± 1[a] | 32 ± 1[a] | 34 ± 1[a] |
|  | Week 4 | 28 ± 1[a] | 27 ± 1[ab] | 23 ± 1[bc] | 24 ± 2[abc] | 22 ± 1[c] | 22 ± 1[bc] |
|  | Week 7 | 33 ± 2[a] | 32 ± 1[a] | 22 ± 1[b] | 27 ± 3[ab] | 21 ± 2[b] | 23 ± 2[b] |
| Fat:Lean (%) | Baseline | 9.2 ± 0.4[b] | 9.2 ± 0.8[b] | 13.1 ± 0.7[a] | 13.3 ± 0.5[a] | 11.7 ± 0.5[a] | 12.6 ± 0.6[a] |
|  | Week 4 | 8.9 ± 0.7[a] | 8.0 ± 0.4[ab] | 7.1 ± 0.5[b] | 7.2 ± 0.7[b] | 6.5 ± 0.5[b] | 6.9 ± 0.5[b] |
|  | Week 7 | 9.7 ± 0.7[a] | 9.0 ± 0.4[ab] | 6.2 ± 0.4[c] | 7.2 ± 1.0[bc] | 6.0 ± 0.6[c] | 6.6 ± 0.7[c] |

[†]Measurements presented were obtained in vivo with an EchoMRI-700 ™ whole body QMR instrument. Data are expressed as means ± SE (n = 9-10/group). For means at the same time point, different superscript letters represent significant differences (p < 0.05).

TABLE 6

| Lentil sample | soaked | heated | Freeze-dry/extrude | ORAC (TE/100 g) | Particle size (% 60 mesh) |
|---|---|---|---|---|---|
| Batch 1 | — | — | milled | 77300 | 12.9 |
| Batch 1 | — | — | Extruded | 85696 | 47.3 |
| Batch 2 | N | N | Freeze-dry | 6356 | 37.2 |
| Batch 2 | Y | N | Freeze-dry | 31348 | 25.3 |
| Batch 2 | N | Y | Freeze-dry | 7768 | 32.8 |
| Batch 2 | Y | Y | Freeze-dry | 4024 | 35.7 |
| Batch 2 | — | — | Extruded | 73416 | 70.9 |
| Batch 2 | — | — | Extruded + water | 51620 | 51.0 |
| Batch 2 >60 mesh | Y | Y | Freeze-dry | 2356 | 100 |
| Batch 2 <60 mesh | Y | Y | Freeze-dry | 6516 | 100 |
| Whole | | | | 9528 | n/a |
| Cotyledon | | | | 2276 | n/a |
| hull | | | | 2744 | n/a |

Oxygen Radical Absorbance Capacity (ORAC) values and particle size for lentil hull prepared via different methods. Powder was prepared by milling after freeze-drying or by extrusion. All samples were subsequently applied to a 60 mesh screen to separate the powder according to particle size prior to extraction, and the percentage that passed through the screen recorded. A sample of each powder was extracted at 25 mg/mL with 50% acetone for 1 hour and the antioxidant activity of each extract was determined by the method of Huang et al [J Agric Food Chem 2002, 50:4437-4444] using a standard curve of 6.25 µM-50 µM Trolox. Two distinct batches were compared with hulls prepared from lentils obtained from different sources. The values are expressed in standard units—Trolox equivalents (TE)/100 g powder.

The invention claimed is:

1. A method for restoring arterial compliance in an individual in need of such treatment, said method comprising administering to the individual an effective amount of a composition comprising a powder made from lentil hulls or a powder made from whole, hulled lentils, wherein the composition is administered over a period of time that is effective for treatment.

2. The method according to claim 1 wherein the composition is made from whole, hulled lentils.

3. The method according to claim 1 wherein the composition is made from lentil hulls.

4. The method according to claim 1 wherein the composition is made from a lentil milling fraction.

5. The method according to claim 1 wherein the composition is administered as a capsule or tablet.

6. The method according to claim 1 wherein the composition is administered as an ingredient in a food product.

7. The method according to claim 1 wherein the composition is administered as a powder suspended in a liquid vehicle.

8. The method according to claim 1 wherein the individual is an individual who is over 55.

9. The method according to claim 1 wherein the individual suffers from more than one chronic condition selected from the group consisting of: cardiovascular disease, diabetes, hypertension, hyperlipidemia, obesity, rheumatoid arthritis and renal dysfunction.

10. The method according to claim 1 wherein the individual is an individual who has a brachial-ankle Pulse Wave Velocity (ba-PVW) above 18 m/s or a carotid-to-femoral Pulse Wave Velocity (cf-PWV) above 10 m/s.

11. The method according to dam 1 wherein the individual is an individual who has an augmentation index normalized at 75/min, heart rate (Alx@75) value of greater than 40%.

12. The method according to claim 1 wherein the effective amount is 250 mg 1 g of lentil hulls.

13. The method according to claim 1 wherein the effective amount is equivalent to 250 mg 1 g of lentil hulls.

14. The method according to claim 13 wherein the effective amount is administered daily.

15. The method according to claim 13 wherein the effective amount is administered daily for 4-12 weeks.

16. The method according to claim 13 wherein the effective amount is administered as two or more doses over the course of the day.

17. The method according to claim 1 wherein, once the arterial compliance has been restored, the arterial compliance is maintained by administering to the individual a maintenance dose of the composition comprising lentil hulls.

18. The method according to claim 17 wherein the maintenance amount is equivalent to 125 mg-500 mg of lentil hulls.

* * * * *